(12) United States Patent
Murdock et al.

(10) Patent No.: US 9,662,558 B2
(45) Date of Patent: May 30, 2017

(54) COMPUTERIZED SMART GAMING TOURNAMENT SYSTEM FOR THE INTERNET

(76) Inventors: Wilbert Quinc Murdock, Bronx, NY (US); Philip Alister Williams, Salt Point, NY (US)

(*) Notice: Subject to any disclaimer, the term of this patent is extended or adjusted under 35 U.S.C. 154(b) by 1187 days.

(21) Appl. No.: 12/799,529

(22) Filed: Apr. 26, 2010

(65) Prior Publication Data

US 2011/0082571 A1  Apr. 7, 2011

Related U.S. Application Data

(62) Division of application No. 09/570,233, filed on May 12, 2000, now Pat. No. 7,789,742.

(Continued)

(51) Int. Cl.
*A63B 69/36* (2006.01)
*A63B 24/00* (2006.01)
*A63B 67/02* (2006.01)
*A63B 63/00* (2006.01)
*A63B 71/06* (2006.01)
(Continued)

(52) U.S. Cl.
CPC .......... *A63B 69/36* (2013.01); *A63B 24/0006* (2013.01); *A63B 24/0021* (2013.01); *A63B 24/0084* (2013.01); *A63B 67/02* (2013.01); *A63B 69/3614* (2013.01); *A63B 24/0062* (2013.01); *A63B 24/0075* (2013.01); *A63B 57/357* (2015.10); *A63B 57/40* (2015.10); *A63B 63/00* (2013.01); *A63B 69/3632* (2013.01); *A63B 69/3655* (2013.01); *A63B 69/3658* (2013.01); *A63B 69/3676* (2013.01); *A63B 69/3685* (2013.01); *A63B 69/3688* (2013.01); *A63B 71/0616* (2013.01); *A63B 71/0622* (2013.01); *A63B 71/0686* (2013.01); *A63B 2024/0034* (2013.01); *A63B 2024/0037* (2013.01); *A63B 2024/0056* (2013.01); *A63B 2024/0068* (2013.01); *A63B 2071/063* (2013.01); *A63B 2071/065* (2013.01); *A63B 2071/0647* (2013.01); *A63B 2220/00* (2013.01); *A63B 2220/13* (2013.01); *A63B 2220/16* (2013.01); *A63B 2220/30* (2013.01); *A63B 2220/62* (2013.01); *A63B 2220/801* (2013.01); *A63B 2220/833* (2013.01); *A63B 2220/89* (2013.01);

(Continued)

(58) Field of Classification Search
CPC ............ A63B 57/0056; A63B 24/0003; A63B 24/0006; A63B 69/36; A63B 69/3614; A63B 24/0021; A63B 24/0084; A63B 69/3632; A63B 69/3655; A63B 69/3658; A63B 69/3676; A63B 69/3685; A63B 69/3688; A63B 71/0616; A63B 2220/83; A63B 2220/833
USPC ................................ 473/180, 199, 222, 353
See application file for complete search history.

(56) References Cited

U.S. PATENT DOCUMENTS 5,209,483 A * 5/1993 Gedney et al. ............... 473/223
5,245,537 A * 9/1993 Barber ......................... 473/403
(Continued)

*Primary Examiner* — William H McCulloch, Jr.
(74) *Attorney, Agent, or Firm* — Howard Eichenblatt, Esq.

(57) ABSTRACT

A system comprising contact and motion sensors adapted to sports equipment and coupled to a computer for the wireless communication of performance data. The computer is connected to a display for the visual simulation of player performance information and may be connected to other computers, thereby permitting competitive play among remote players.

10 Claims, 15 Drawing Sheets

Related U.S. Application Data

(60) Provisional application No. 60/133,722, filed on May 12, 1999.

(51) Int. Cl.

| | | |
|---|---|---|
| *A63F 9/24* | (2006.01) | |
| *A63B 57/40* | (2015.01) | |
| *A63B 57/30* | (2015.01) | |

(52) U.S. Cl.

CPC ....... *A63B 2225/20* (2013.01); *A63B 2225/50* (2013.01); *A63F 9/24* (2013.01)

(56) References Cited

U.S. PATENT DOCUMENTS

| | | | | |
|---|---|---|---|---|
| 5,507,485 | A * | 4/1996 | Fisher | 473/407 |
| 5,700,204 | A * | 12/1997 | Teder | 473/199 |
| 5,884,913 | A * | 3/1999 | Cohen | 473/154 |
| 6,073,086 | A | 6/2000 | Marinelli | 702/141 |
| 6,254,492 | B1 * | 7/2001 | Taggett | 473/219 |
| 6,336,891 | B1 * | 1/2002 | Fedrigon | A63B 22/02 |
| | | | | 434/247 |
| 7,095,312 | B2 * | 8/2006 | Erario et al. | 340/323 R |
| 7,321,330 | B2 * | 1/2008 | Sajima | 342/59 |
| 7,789,742 | B1 * | 9/2010 | Murdock | A63B 24/0021 |
| | | | | 273/108 |
| 7,789,767 | B2 * | 9/2010 | Lindsay | 473/251 |
| 8,002,645 | B2 * | 8/2011 | Savarese et al. | 473/353 |
| 8,257,189 | B2 * | 9/2012 | Koudele et al. | 473/155 |
| 8,425,350 | B2 * | 4/2013 | Savarese et al. | 473/353 |
| 8,861,091 | B2 * | 10/2014 | French | A63B 24/0003 |
| | | | | 359/629 |
| 9,028,338 | B2 * | 5/2015 | Chiono | A63B 69/3661 |
| | | | | 473/226 |
| 9,457,228 | B2 * | 10/2016 | Sinha | H04N 5/772 |
| 2007/0167247 | A1 * | 7/2007 | Lindsay | 473/131 |
| 2008/0076580 | A1 * | 3/2008 | Murdock et al. | 463/42 |
| 2008/0188310 | A1 * | 8/2008 | Murdock | 463/42 |
| 2009/0036237 | A1 * | 2/2009 | Nipper et al. | 473/409 |
| 2011/0081978 | A1 * | 4/2011 | Murdock et al. | 473/191 |
| 2011/0082571 | A1 * | 4/2011 | Murdock et al. | 700/92 |
| 2011/0087344 | A1 * | 4/2011 | Murdock et al. | 700/91 |
| 2011/0092260 | A1 * | 4/2011 | Murdock et al. | 463/3 |
| 2011/0130223 | A1 * | 6/2011 | Murdock et al. | 473/409 |
| 2011/0151977 | A1 * | 6/2011 | Murdock et al. | 463/42 |
| 2011/0212757 | A1 * | 9/2011 | Murdock et al. | 463/2 |
| 2011/0281621 | A1 * | 11/2011 | Murdock et al. | 463/3 |
| 2012/0220385 | A1 * | 8/2012 | Richardson et al. | 473/156 |
| 2014/0297007 | A1 * | 10/2014 | Voutilainen | A63B 24/0003 |
| | | | | 700/91 |
| 2016/0354660 | A1 * | 12/2016 | Kostuj | G09B 19/0038 |
| 2016/0361592 | A1 * | 12/2016 | Isogawa | A63B 24/0003 |
| 2017/0004729 | A1 * | 1/2017 | Kano | G09B 19/0038 |

* cited by examiner

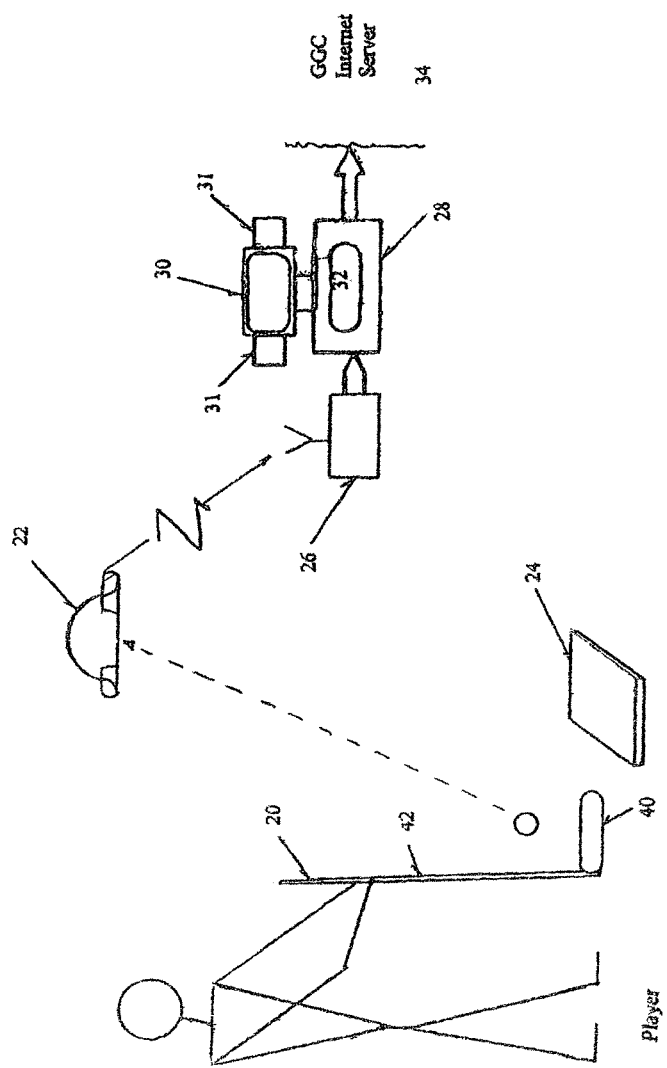
FIGURE: 1

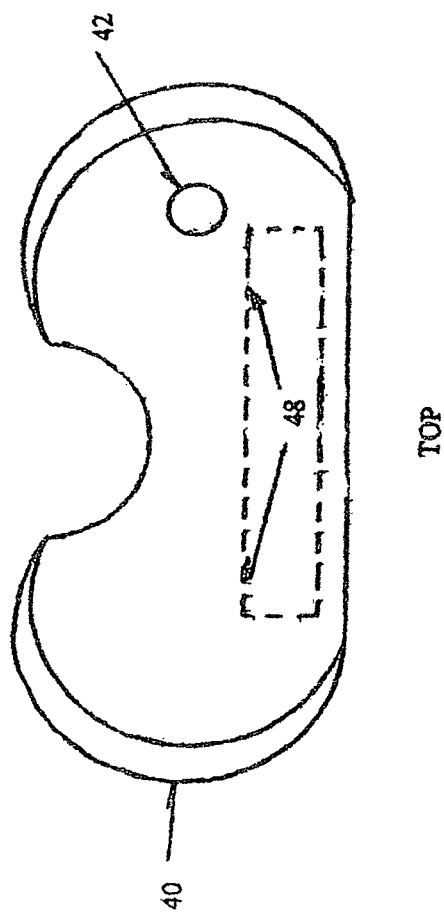
FIGURE: 2
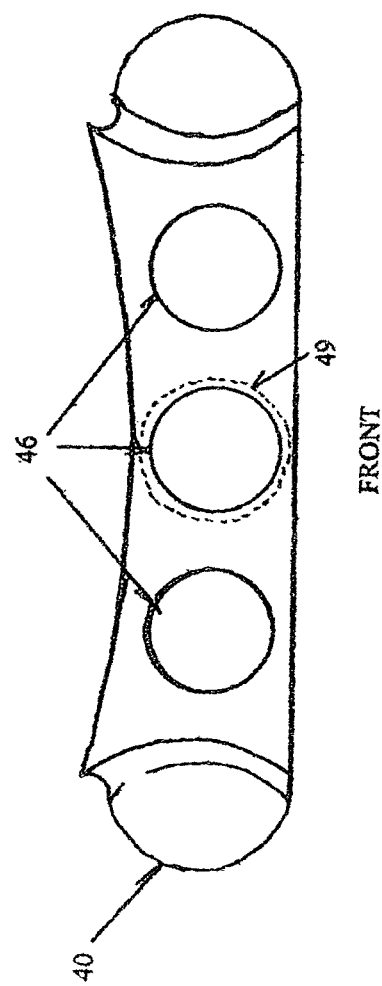
FIGURE: 3

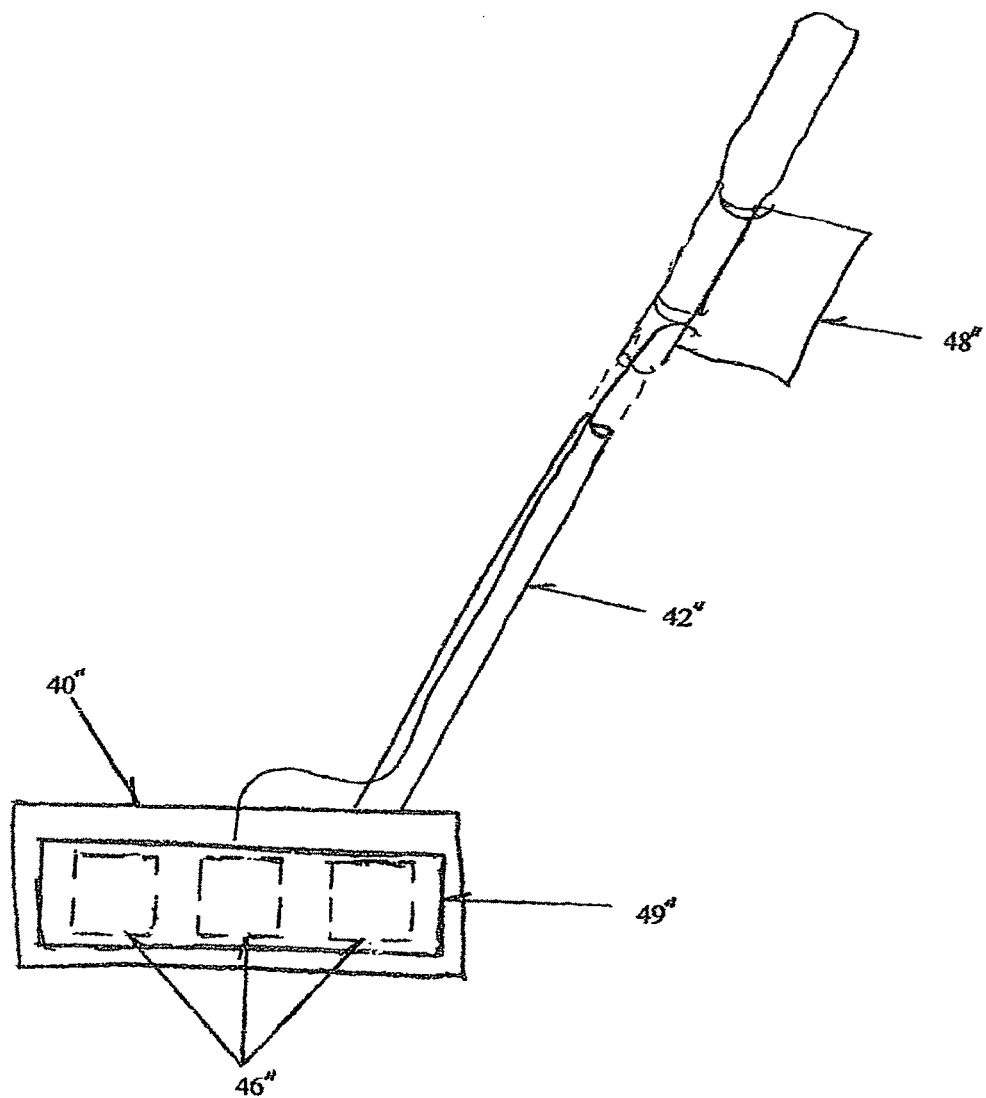
FIGURE: 4

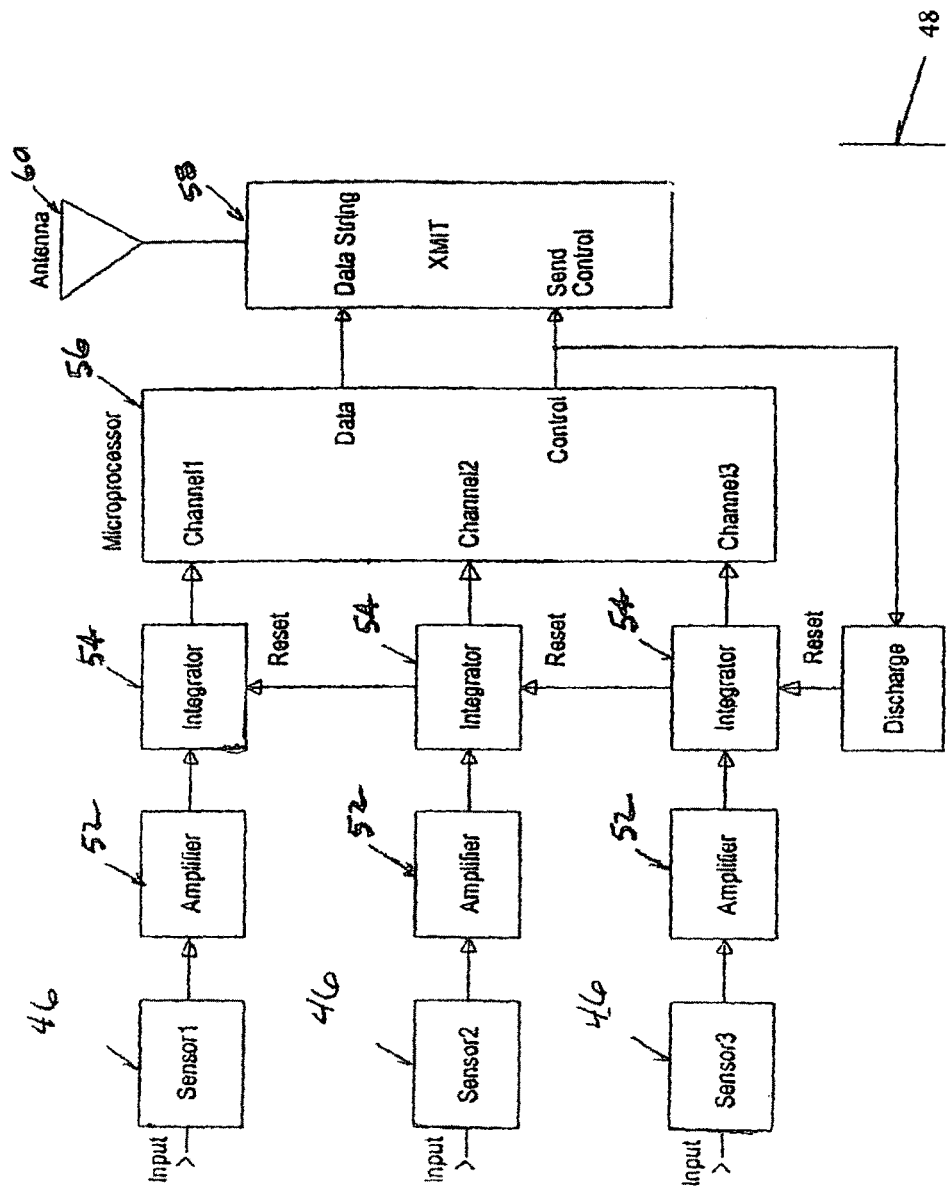
FIGURE: 5

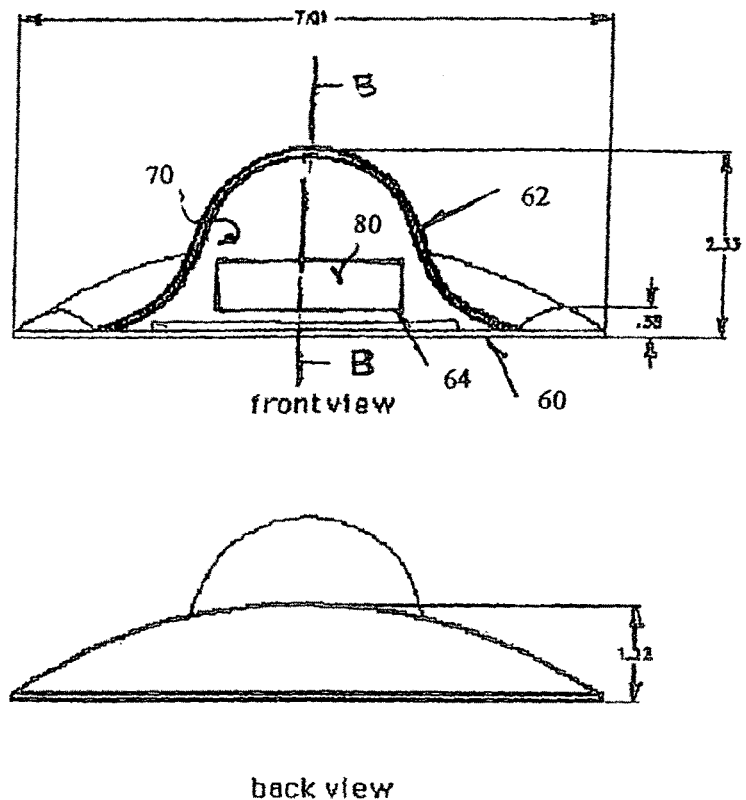
FIGURE: 6A

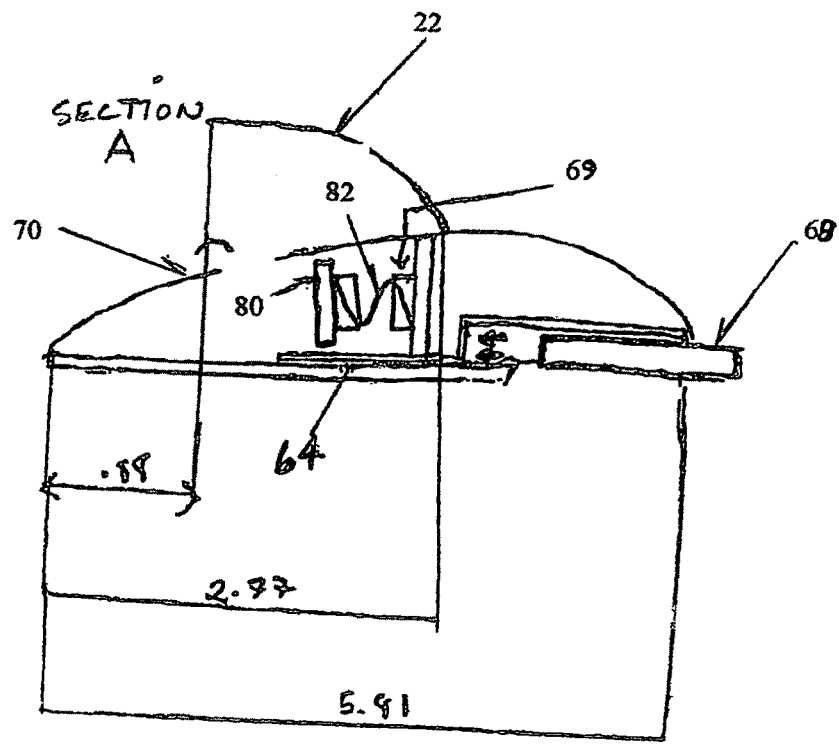
FIGURE: 6B

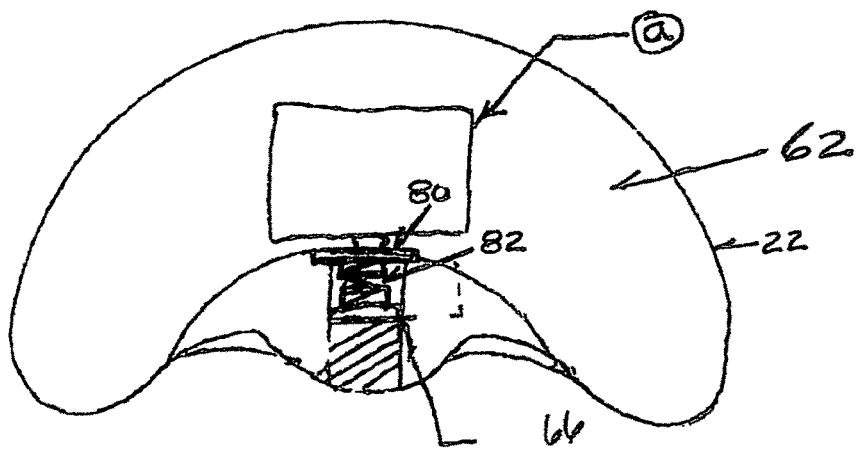
Top view with components exposed
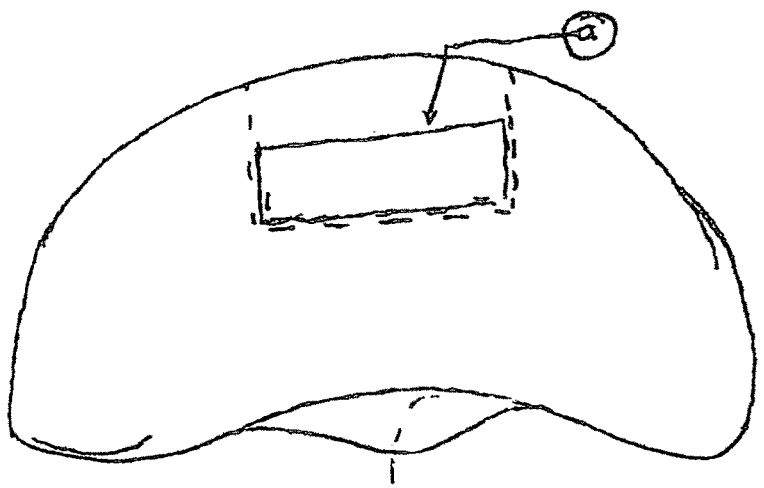
(a) Bottom view with electronics in position
FIGURE: 6C

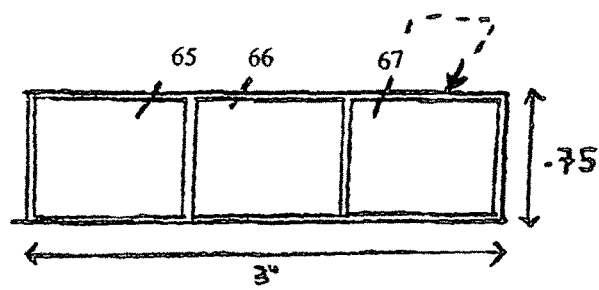
Tripad Sensor with three different activation areas
FIGURE: 7

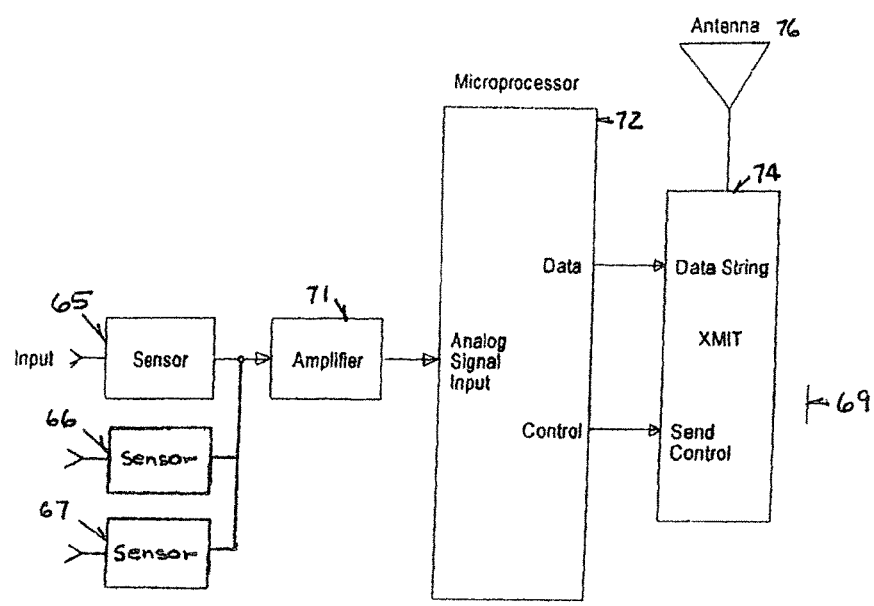
FIGURE: 8

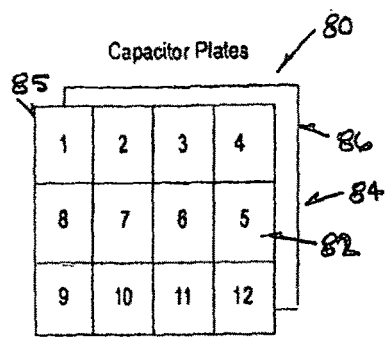
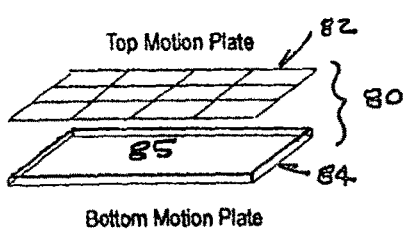
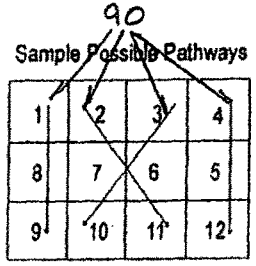
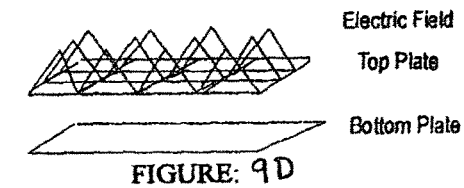
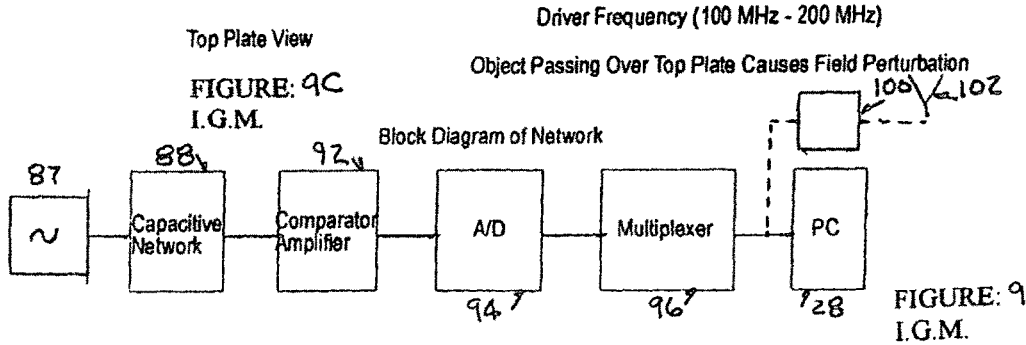

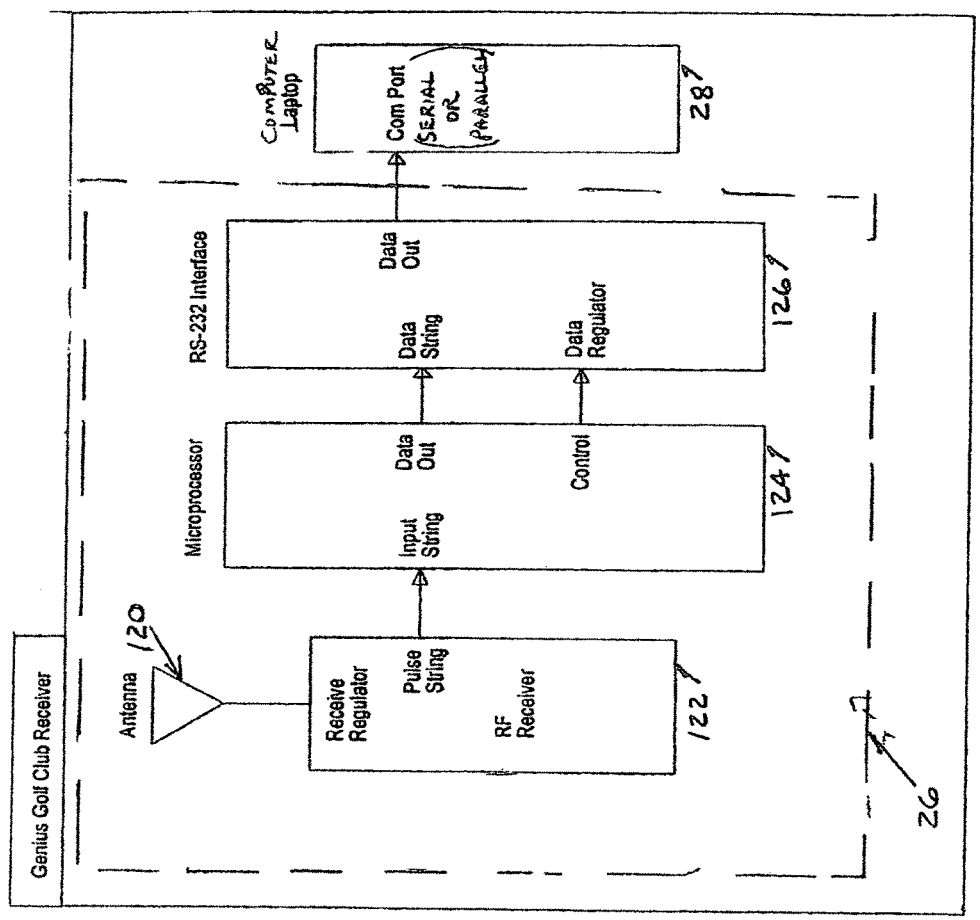
FIGURE: 10

Visual Gaming Software Process Flow Diagram
Confidential

Client-Server Process Flow Diagram

Visual Golf Software Process Flow Diagram
Confidential

COMPUTERIZED SMART GAMING TOURNAMENT SYSTEM FOR THE INTERNET

CROSS REFERENCE TO RELATED APPLICATION

Priority is claimed from U.S. Provisional Ser. No. 60/13,722, filed May 12, 1999 for all subject matter common hereto. That provisional application is incorporated by reference herein. This is a divisional application and the parent application for this divisional application is, Ser. No. 09/570,233 filed May 12, 2000 now U.S. Pat. No. 7,789,742.

REFERENCE TO MICROFICHE APPENDIX

A microfiche appendix including 1 microfiche with 27 frames accompanies and forms a part of this application.

FIELD OF INVENTION

This invention relates to a smart gaming system coupling sports implements and a computer. More particularly, this invention relates to a system wherein a golf club or other sports implements communicate wirelessly to a personal computer and thereby to the internet for competitive tournament play. Players are grouped together by an internet server and once play ensues the internet server stores only player information whereby one player is then designated as the server and the other players as clients.

BACKGROUND OF THE INVENTION

This system stores a queue of awaiting players and groups players together via an internet server for purposes of tournament game play. However, once play ensures the internet server retains only remote player address and sport information and designates one player's computer within the group at a remote site to function as the server and the other players as clients. This results in remote tournament play devoid of a single internet server having to store information about each game of a particular sport in progress that can result in cycle time delays and player disconnects due to internet server capacity issues.

It is desirable to remotely communicate actual player performance location, whereby more sophisticated analysis and prediction possibilities are realizable via computer technology and state-of-the-art display techniques. Further, it is also desirable to use such performance information in an expanded capacity to provide interactive competitive play among numerous players in locations remote from each other.

SUMMARY OF INVENTION

This invention relates to a system that interconnects a golf club or other sports implements to a computer. In a preferred embodiment the computer is coupled wirelessly to a sports implement component. Further, the invention, with components summarized below, allows participants to be paired or grouped together to enter into a competition against each other. Each player asks the computer who is available to play a contest via the internet. Once a players pairs up against another player anywhere in the world and play ensues, the computer and display show each participant's score via animation or graphics that preferably relate to a player's individual performance statistics. A single player may play without an opponent to practice and improve basic golfing skills using the computer and display to track performance.

The system application is unlimited. Much of this system can be used not only for golfing competition on the Internet, but for other sports as well. Sports implements other than golf clubs, swing detectors and receptacles can be outfitted with sensors according to this invention and used for training purposes, rehab, or for interactive internet competition.

The technology can be used for training, competition, and the improvement of player reflexes and coordination. With little or no modification, the technology has applications in any competitive sport.

1. Smart Golf Club

A wireless golf club is constructed to contain or alternatively, a standard golf club is modified to contain, a multiple sensor or transducer array located on the club head at the face or hitting surface. Upon impact of the head of the club with a golf ball, the impacted sensors produce detectable variances representing the magnitude and duration of the club-ball impact force and the proximate location of such contact relative to the preferred location, the "sweet spot", on the face of the club head. The variances are electronically processed into digitally coded information and remotely transmitted by an electrical communication circuit either contained within or attached to the golf club.

In each golf club device and golf ball receptacle device according to this invention, in a preferred embodiment the transducers are or include piezoactive elements and or pressure sensors. As used herein, "piezoactive" includes piezoelectric and piezoresistive components. Piezoactive components are defined as components the electrical properties of which, when the component is subjected to physical force, vary.

The smart golf club system uses biofeedback to create an intelligent golf training and entertainment system. The smart golf club system is a diagnostic and analysis tool used to improve a player's skills by relatively instantaneous visual cues and acoustic feedback with little or no human intervention. The smart golf club system takes the generated data and reconstructs it into a useful visual format that can be presented in a variety of ways including 3-dimensional animation.

The smart golf club system integrated circuit or circuits can be located anywhere within the club including the head and or shaft.

The smart golf club has a means via its built in microcontroller to process, analyze, store, hitting pattern data and transmit it to the computer and or the Internet for further analysis. In playback mode the smart golf club system memorizes how many times each sensor was hit. This provides the golfer information about his or her hitting pattern. Using a computer algorithm, we can analyze and calculate a hitting pattern and having a personalized sports hitting detection system for each athlete.

2. Golf Ball Receptacle

A ball receptacle has an open end to receive a golf ball and contains a transducer located so as to sense the ball entering receptacle. Upon impact with the golf ball, the sensor produces a detectable variance representing impact with the ball. The variance is electronically processed into display coded information and remotely transmitted by an electrical communication circuit. In one preferred embodiment the communication circuit is contained within the receptacle. Preferably the communicate circuit for the receptacle is a radio frequency transmitter. The receptacle can either be designed for indoor use or can be a cup in an actual green with the communication circuit housed in the cup or elsewhere.

In each of the golf club device and golf ball receptacle device according to this invention, in a preferred embodiment the transducers are or include piezoactive elements. As used herein, "piezoactive" includes piezoelectric and piezoresistive components. Piezoactive components are defined as components the electrical properties of which, when the component is subjected to physical force, vary.

3. Golf Club Motion Sensor Plate

A golf club swing motion sensing device contains an array of uniformly distributed sensing transducers upon or proximate to the device surface. This motion sensing device may be formed as a mat, a plate, or other substantially flat surface from which a golf ball is hit. The transducers produce detectable varying characteristics such as capacitance representing the velocity, angle, and proximity of a golf club relative to the surface of the device. The variances are electronically processed into digitally coded information and remotely transmitted by an electrical communication circuit contained within or electronically connected to the device.

4. Wireless Signal Receiver and Computer

At each remote player site, wireless radio frequency equipment receives the digitally coded transmitted signals from the golf club, the golf ball receptacle, and the club swing motion sensing device. The signals are demodulated and processed into serial binary data suitable for communications to the computer via either serial or parallel ports. As the game progresses, the computer under the control of the golfing software, monitors and directs the flow of communications between the players via the internet and displays the game simulations and performance information.

5. Computer Golfing Software System

At each remote player site, a computer under the control of the golfing software, monitors and controls the sequential play of the game and interacts with the player at the site and also competing players at the other remote sites via the internet. The software system generates the game simulations for display and tracks each player's performance as the game progresses.

The above and further features and advantages of the invention will be better understood with reference to the accompanying drawings and the following detailed description of preferred embodiment.

BRIEF DESCRIPTION OF THE DRAWINGS

FIG. 1 is a diagrammatic illustration of components of a computer implemented golf system according to this invention.

FIG. 2 is a top plan view of a golf club with sensors and circuitry and used in the computer implemented system of FIG. 1.

FIG. 3 is front elevation view of the golf club head of FIG. 2, and shows three sensors located at the face of the club head.

FIG. 4 is a diagrammatic front plan view of a putter with a club head and circuitry forming a further, alternative embodiment of a club for use with the computer implemented system of FIG. 1.

FIG. 5 is a schematic block diagram of a club head electronics installation for use with the club heads of FIGS. 2-4.

FIG. 6A is a front elevation view of a golf ball receptacle for use with the system of FIG. 1.

FIG. 6B is a cross-sectional view along the lines B-B of FIG. 6A.

FIG. 6C is a fragmentary top plan view of the receptacle of FIGS. 6A and 6B illustrating internal components of the receptacle.

FIG. 7 is a top plan view of a golf ball sensing element with three distinct activation areas for use in the receptacle of FIGS. 6A-6C.

FIG. 8 is a schematic block diagram of a receptacle electronics installation for communicating with the computer in a computer implemented system according to FIG. 1.

FIGS. 9A-9D are diagrammatic illustrations of a golf club motion or swing sensor plate for use with the system according to FIG. 1.

FIG. 9E is a block diagram of electronics used in association with the swing sensors plate of FIGS. 9A-9D.

FIG. 10 is a block diagram of a computer installation for use as the computer and information receiving interconnect of the system of FIG. 1.

DETAILED DESCRIPTION OF PREFERRED EMBODIMENT

Figure 3A:
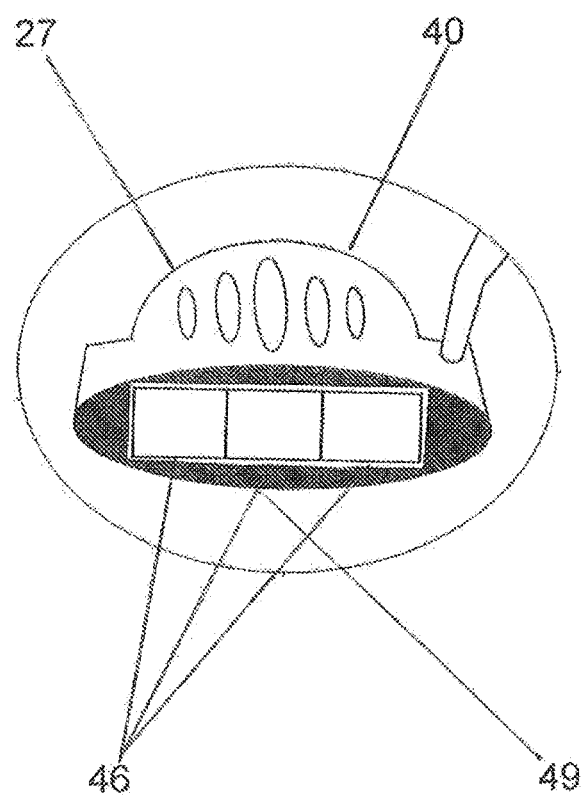
FIG. 3A is a front plan view of a further embodiment of a club head for use with the computer implemented golf system of FIG. 1.

As shown in FIG. 1, a preferred embodiment of the invention includes a wireless smart golf club 20, a wireless golf ball receptacle 22, a wireless golf club motion sensing plate 24, a wireless receiver 26 connected to a computer 28, and a display or monitor 30 with speakers 31 operated under the control of golf system software 32, and connected via the internet to an internet golf game server 34 (called herein the GGC server)

1. Smart Golf Club

The smart golf club 20 has a head 40 and a shaft 42. As shown in FIGS. 2 and 3, the head 40 has a shaft opening 42, a plurality of embedded contact sensors 46 (three are illustrated in the preferred embodiment), and the internal electronics circuitry 48 including a wireless radio frequency transmitter (58 in FIG. 5). As shown, at least one of the sensors 46 is located at or proximate to the optimal location on a club face 47 for contact with the golf ball, the "sweet spot" 49. The remaining two sensors are adjacent and on either side of the sweet spot 49. The contact sensors may be, but are not limited to sensors employing piezoactive type transducers, specifically, either piezo-electric or piezo-resistive transducers (similar, but is not limited to the Cooper Instruments LPM 562).

In an alternative embodiment, FIG. 3A, three sensors 46 are applied to the face of an adapted club by a Mylar tape or other means 49. Again, the electronic circuitry is internal to the club head 40 and connects to the sensors 46 by leads 27.

In a second alternative embodiment, to retrofit a standard golf club, contact sensors 46 are part of an adapter 40 attached to an ordinary club head as seen in FIG. 4 and wire connected to an electronic circuitry 48 attached to the club shaft 42 or elsewhere on the club.

A golf ball contacting any sensor 46 produces a detectable variance indication the magnitude and duration of sensor-ball impact. The variance may be a change in resistance of a piezo-resistive transducer or a voltage change in the case of a piezo-electric transducer. As shown in FIG. 5, the variance is detected and amplified by an associated amplifier 52 and is the input to an associated integration circuit 54, the output of which represents the energy of the ball-club contact event. Connected to the integration circuit 54, a microprocessor 56 is a multi-input signal processing circuit (similar, but not limited to a Motorola #68HCO5) having analog to digital signal converting circuits (ADCs), one for each input channel, and a sequential digital signal encoding circuit connected so as to convert the ADC outputs into a time multiplexed serial digital data stream containing a binary coded-word for each channel indicating the energy of the associated sensor-ball impact event.

A radio frequency transmitting circuit 58 receives the serial digital data from the microprocessor 56 and wirelessly transmits the information via an internal antenna 60 to a receiver 26 (FIG. 1) for subsequent processing by the computer 28.

2. Golf Ball Receptacle

The golf ball receptacle 22 has a top 62 shaped to allow entry of a golf ball, as shown in FIGS. 6A, 6B, and 6C. The receptacle has a contact sensor pad 64, shown in FIG. 7, containing at least one contact sensor (three different activation areas 65, 66, and 67 are illustrated in the preferred embodiment), a ball return mechanism 69 (FIG. 6B) and internal electronic circuitry 68 (FIG. 6B). The internal circuitry includes a wireless radio frequency transmitter (not separately shown in FIGS. 6A, B and C). As shown, the preferred embodiment has contact sensor pad 64 positioned within the receptacle 60 such that the center activation area 66 aligns with the center of a ball entry 70. Additional sensor activation area 65 and 67 are adjacent, one on either side of the center area 66. In the preferred embodiment, of FIGS. 6A, 6B, and 6C, and like the sensor used at the face of the club, the sensors may be, but are not limited to, sensors employing piezo-active type transducers, specifically, either piezo-electric or piezo-transducers.

A golf ball entering the receptacle 60 and containing the sensor pad 65, 66 or 67 produces a detectable variance indicating the ball entry event. The variance may be a change in resistance in the case of a piezo-resistive transducer (similar, but not limited to Cooper Instruments LPM 562) or a voltage change in the case of a piezo-electric transducer. As illustrated in FIG. 8, the variance is detected and amplified by an associated amplifier 71. The amplified signal then is input to a microprocessor 72 having an analog to digital signal converting circuit (ADC) and a digital signal encoding circuit connected so as to convert the ADC output representing the sensors signals into a serial digital data stream containing a binary coded word indicating the sensor-ball contact event. The microprocessor 72 may be the same or similar to the microprocessor 56 of the golf club electronics. A radio frequency transmitter circuit 74 receives the serial digital data from the microprocessor 72 and wirelessly transmit' the information via an internal antenna 76 to the receiver 26 (FIG. 1) for subsequent processing by the computer 28.

The ball return mechanism 68 can be simple as a back plate 80 located to be engaged by a golf ball entering the receptacle 22 and supported and biased by a spring or springs 82 to eject the ball. Other known ejection devices, similar to those used in pin ball machines and either mechanically or even electrically activated, can be used to improve the effect if desired.

The receptacle configuration is susceptible to much variation. The receptacle illustrated and described above is well suited to indoor use, on carpet for example. It is clear, however, that an actual cup, installed in an actual green, with real or synthetic grass, can be similarly equipped.

3. Golf Club Motion Sensor Plate

The golf club motion sensor plate 80 having a top motion plate 82 and a bottom motion plate 84 is diagrammatically shown in FIGS. 9A-D, wherein the top motion plate 82 contains a plurality of capacitor-forming electrically isolated platelets 83 (twelve platelets are illustrated in this exemplary preferred embodiment). They are evenly distributed at or just below the top plate's exterior upper surface 82. The bottom plate 84 has a homogenous electrically conductive interior surface 85 underlying the platelets 83. Each capacitive platelet 83 contained in the top motion plate 82 forms a capacitive component when the top and bottom motion plates are vertically closely spaced to form the golf club motion sensor plate. A suitable insulator may be sandwiched between the two plates. The structure is adhesively or otherwise mechanically joined and it may be covered or coated as desired. The result is a golf club motion sensor plate 80 containing a capacitor matrix (a 3×4 capacitor matrix is illustrated in the preferred embodiment0. The capacitive components 83 are connected to form a capacitive network 88 as is indicated in FIG. 9E.

Applying an energizing high frequency alternating electrical signal having a frequency in the range from 100 MHz to 200 MHz from an oscillator 87 to the golf club motion plate capacitive network 88 produces an electromagnetic field above the surface of each platelet 83 of the capacitive components of the motion sensor plate 80. Any object, including a golf club, passing near the surface of the energized motion plate will cause a perturbation of the electromagnetic field as illustrated by the sample possible pathways 90 across the plate in FIG. 9C. A network 92 of electrical comparator amplifiers (FIG. 9B) is connected to the capacitor network. The comparators of the network 92 are connected one to one with the capacitive elements of the capacitive network 88. The comparators of the network 88 detect voltage variations occasioned by electromagnetic field disturbance due to a golf cub moving over certain of the capacitive elements of the motion plate. Each different golf club motion over the energized motion plate will produce a uniquely identifiable signal from the comparator amplifier network. There are a variety of known proximity sensors that could be gathered together in an array like that of the platelets 83 to serve as the transducer portion of the golf club motion detector.

The electrical signal from the comparative amplifier network 92 is applied to an analog to digital signal converter 94 (ADC) and the ADC digitized output signal is converted into a serial digital data stream by a multiplexer 96. This data identifies each platelet having had its field disturbed. The serial digital data can be input directly by wire from a multiplexer 96 to the computer 28 located at the site of the golf player and golf club motion sensor plate 80, or as in the preferred embodiment, illustrated in FIG. 1, the serial data can be transmitted 100 and an antenna 102, included in the golf club motion electronic transmitter communication circuitry from FIG. 1.

The computer 28, under the control of the golf system software, will analyze the serial digital club motion signal, recognize from the transmitted signals the platelets 83 over which the club head passed and display the golf club swing motion.

4. Wireless Signal Receiver and Computer

At each player site, a wireless radio frequency signal receiver 26 is connected to the computer 28 by either the serial (USB) or parallel computer ports, as shown in the functional block diagram, FIG. 10. The wireless signal receiver 26 detects digitally coded radio frequency transmissions from the communication circuit associated with any of a smart golf club 20, a golf ball receptacle 22, or a golf club motion sensing plate 24, as shown in FIG. 1. The received transmission are demodulated by the RF receiver circuitry 122 (FIG. 10) connected to a microprocessor 124, which converts the demodulated data signal to serial binary coded data suitable for communications to a computer 28. The computer 28, under the control of the internally installed golf system software program, monitors and directs the flow of communications between remotely located players via the internet and displays the game simulations and performance information. In appropriate installations the wireless electromagnetic signals that communicate with the receiver may be infrared communications.

5. Computer Golfing Software

Figure 11:
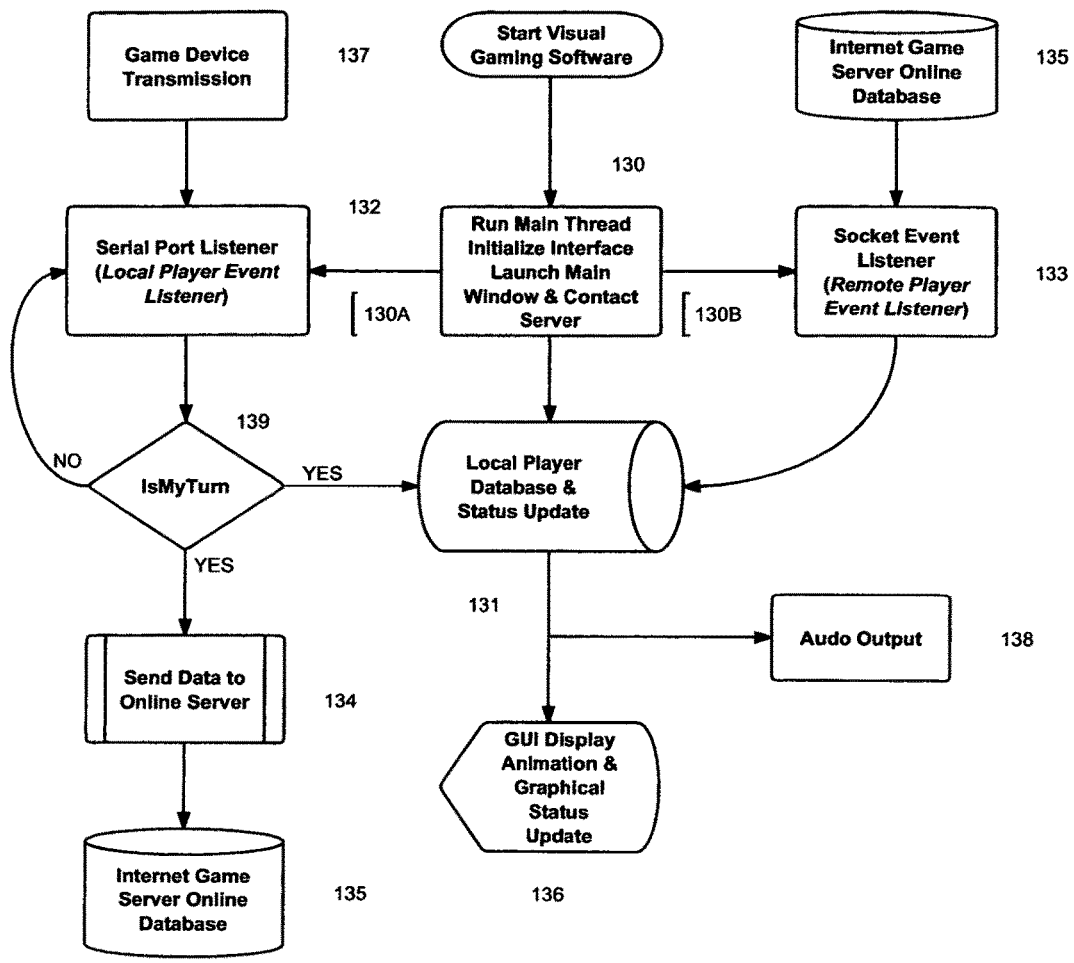
FIG. 11 is a functional block diagram of the software operation of the computer of FIG. 10.

At each remote player site, the computer 28 (FIG. 1) under the control of the golfing software program (shown in the golfing software system functional block diagram, FIG. 11) monitors and control initialization and the sequential play of the golf game, or alternatively, the individual player practice session. Upon start up by a player at a particular site, the system input parameters are set and the system internet and player port interfaces are initialized 130 as indicated by the arrows 130*a* and 130*b*. For internet communications, the serial port listener of the computer 28 is enabled in the preferred embodiment. A remote player event listener is initialized. It will communicate events from one or more of the smart golf club, the golf ball receptacle and the motion sensor plate. The main operational software (program) thread is run 130, and the system awaits data input from the appropriate computer communications ports at 132 (port), 133 (Remote player Socket Event Listener).

Figure 12:
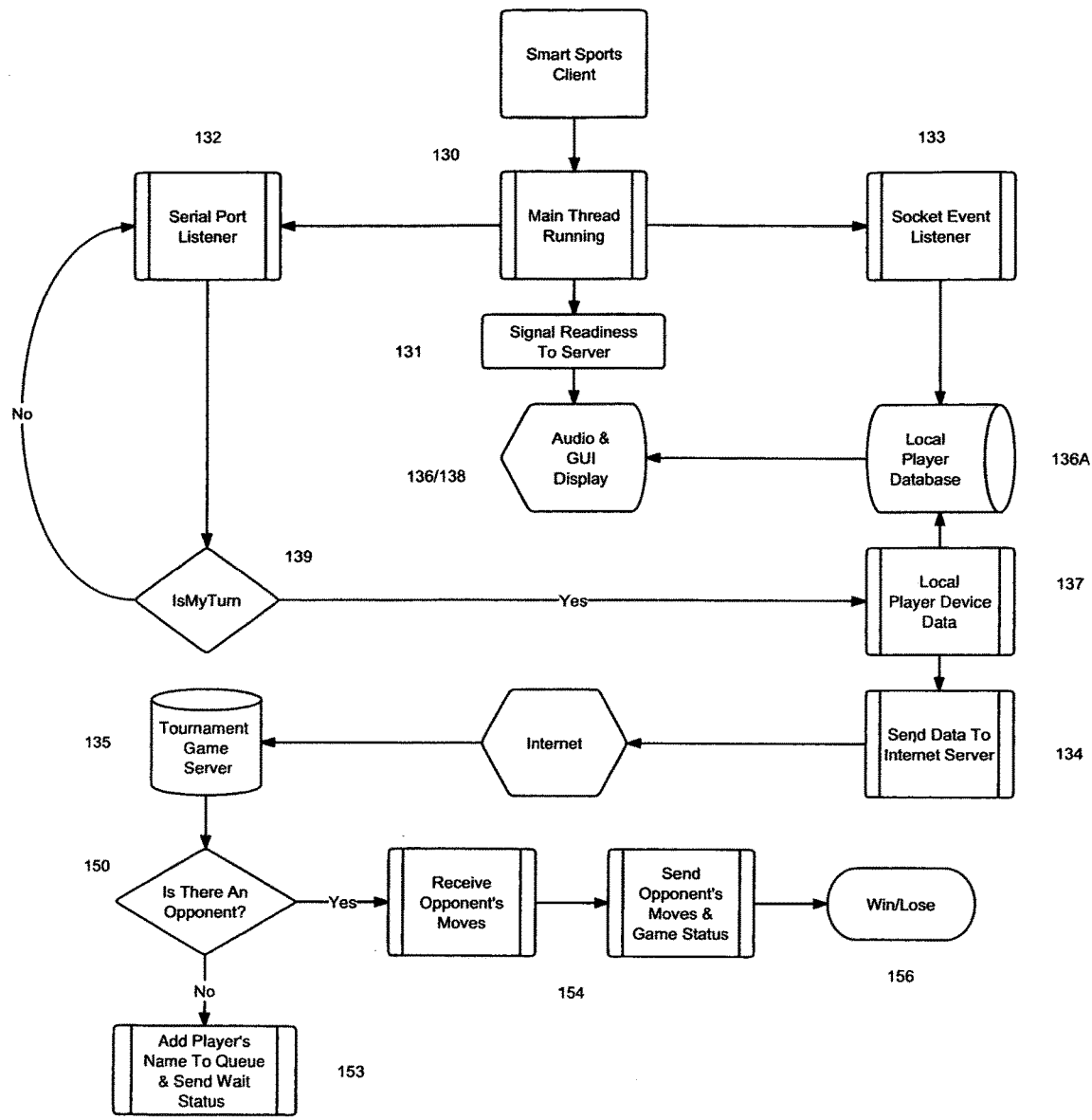
FIG. 12 is a flowchart illustrative of a portion of the operation of the computer of FIG. 10 operating as indicated in the block diagram of FIG. 11.
Figure 13:
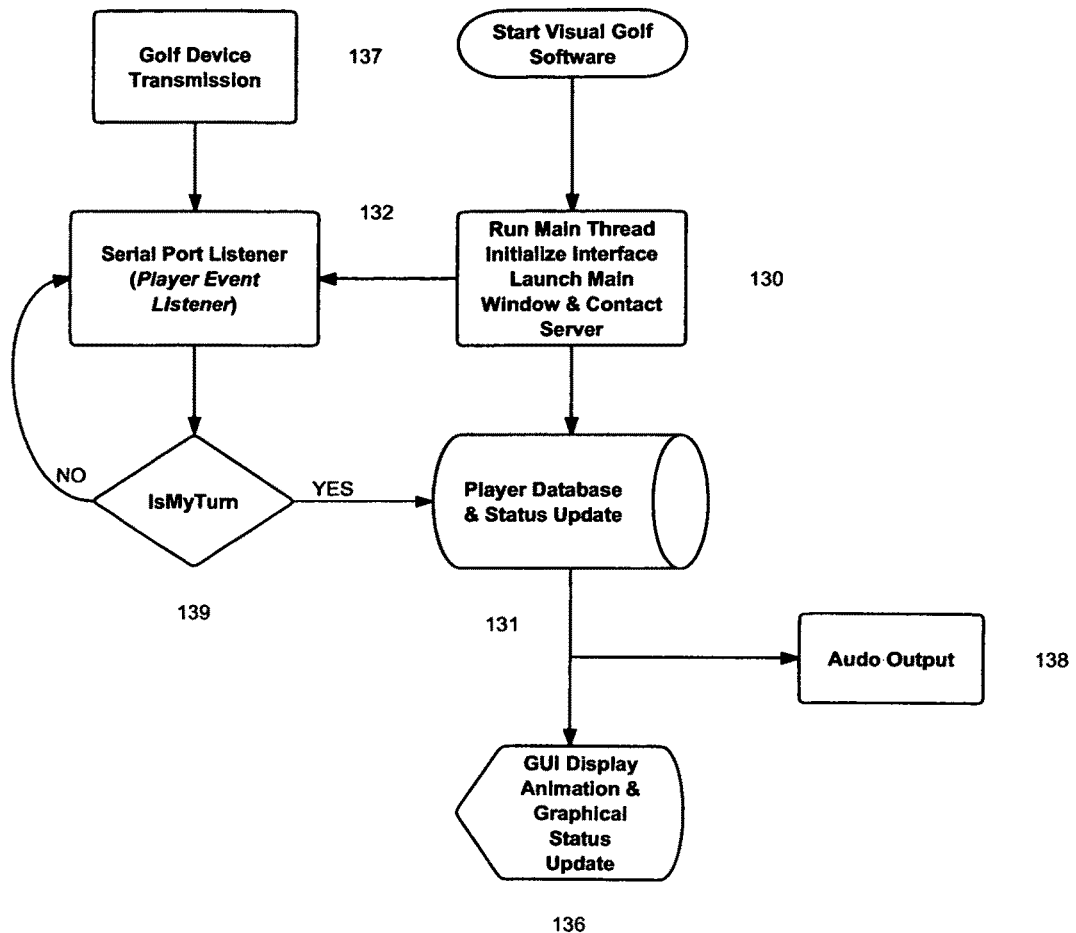
FIG. 13 shows an exemplary system process.

If the competitive play mode has been selected, the program generates a player participation request and sends 134 the request to the GGC game internet server (GGC server) 34 (FIG. 1). Upon identification of a player opponent at 150 (FIG. 12) by the GGC server, the program initiates the player identification sequence 152 and sequential play begins 154 (This software sequence and control routine occurs at each remote site where play has been initiated. During the game play sequences 154, the program generates the appropriate animation, display, and audio data and commands 136 and 138 (FIG. 11), and communicates with the associated display and speaker devices 30 and 31 (FIG. 1). Upon the occurrence of a local player event, detected at 133, the main operating program at 130, displays the event at 136, and communicates the event at 132 by causing a device transmission at 137 to be send at 134 via the internet GGC server 135 which displays the event for the opposing player and alerts the opposing player it is his/her turn to play. The local player event may be, but is not limited to the smart golf club impacting a ball, the swing of a club across the sensing plate or the balls entry into the receptacle. The program contains time delay limits for the player action, and delays of play beyond these limits generate play quit and disconnect signals.

The event at 133 also has the effect of indicating at 139 that it is no longer the local players turn and enables (as indicated by line 139) the serial port listener at 132 to detect an event from the remote player, again via the internet.

If the single player practice mode is selected, the internet communications sequences are disabled, other software sequential operating routines continue as above described and the players golf club stroke, ball-receptacle contact, and/or club swing motion sensor information are communicated only to the computer located at the players site and the performance information analyzed and displayer only at the local players site.

When a game is won, lose, or terminated, the golf software system generates the appropriate output signals 156 (FIG. 12), displays the player performance information, and resets to initial pre-game conditions. If one player opponent quits the game or is "timed out" (due to excessive delay in play) and the remaining player wishes to continue play, the software resumes an internet search for another opponent 152 and 153.

Using programming as contained in the accompanying microfiche appendix, one skilled in the art can readily accomplish the game programming described. Alternative programming too will be apparent from the foregoing functional description and the illustrations contained in the appended drawings While a preferred embodiment has been described, it will be appreciated that many variations and modifications in the system, its operation, and its various components may be made without departure from the spirit and scope of invention as set forth in the appended claims.

What is claimed is:

1. A system including a server, a host processor, and a network of game systems, each game system comprising:

a ball receptacle, a motion sensing device, a sports implement, a speaker, a display device, a processor, and a wireless signal receiver;

the ball receptacle comprising an open end configured to receive a ball, a contact sensor, a first amplifier, and a first analog-to-digital converter, the contact sensor configured to transmit contact data to the first amplifier, the first amplifier configured to receive contact data from the contact sensor and transmit amplified contact data to the first analog-to-digital converter, and the first analog-to-digital converter configured to receive amplified contact data from the first amplifier and transmit digital contact data to the wireless signal receiver;

the motion sensing device comprising a plurality of electrically isolated capacitors, an electrically conductive interior surface, an insulating layer, a variance detection member, a second amplifier, and a second analog-to-digital converter, the insulating layer disposed between the plurality of electrically isolated capacitors and the electrically conductive interior surface, the second amplifier configured to receive motion data from the variance detection member and transmit amplified motion data to the second analog-to-digital converter, and the second analog-to-digital converter configured to receive amplified motion data from the second amplifier and transmit digital contact data to the wireless signal receiver;

the sports implement comprising a hitting surface, a third amplifier, and a third analog-to-digital converter, the hitting surface comprising a transducer array, the transducer array including one or more piezoelectric elements, the transducer array configured to transmit contact data to the third amplifier, the third amplifier configured to receive contact data from the contact sensor and transmit amplified contact data to the third analog-to-digital converter, and the third analog-to-digital converter configured to receive amplified contact data from the third amplifier and transmit digital contact data to the wireless signal receiver;

the processor programmed to receive digital motion data and digital contact data from the wireless signal receiver, analyze the digital motion data and the digital contact data received from the wireless signal receiver, transform the digital motion data and the digital contact data into graphic data, sound data, and performance data, transmit the sound data to the speaker, transmit the graphic data to the display device, and transmit the performance data to the server; and the server configured to transfer local player events from a remote player site to another remote player site for presentation to another player, transmit turn notification data to remote player sites, receive and measure player time delays, disconnect player remotes sites with excessive time delays, conduct internet search for additional player remote sites.

2. A system including a sports implement, a speaker, a processor, and a wireless signal receiver;

the sports implement comprising a hitting surface, a third amplifier, and a third analog-to-digital converter, the hitting surface comprising a transducer array, the transducer array including one or more piezoelectric elements, the transducer array configured to transmit contact data to the third amplifier, the third amplifier configured to receive contact data from the contact sensor and transmit amplified contact data to the third analog-to-digital converter, and the third analog-to-digital converter configured to receive amplified contact data from the third amplifier and transmit digital contact data to the wireless signal receiver;

the processor programmed to receive digital motion data and digital contact data from the wireless signal receiver, analyze the digital motion data and the digital contact data received from the wireless signal receiver, transform the digital motion data and the digital contact data into performance data, and transmit the performance data to a server; and the server configured to transfer local player events from a remote player site to another remote player site for presentation to another player, transmit turn notification data to remote player sites, receive and measure player time delays, disconnect player remotes sites with excessive time delays, and conduct as internet search for additional player remote sites.

3. The system of claim 2, further including a ball receptacle, the ball receptacle comprising an open end configured to receive a ball, a contact sensor, a first amplifier, and a first analog-to-digital converter, the contact sensor configured to transmit contact data to the first amplifier, the first amplifier configured to receive contact data from the contact sensor and transmit amplified contact data to the first analog-to-digital converter, and the first analog-to-digital converter configured to receive amplified contact data from the first amplifier and transmit digital contact data to the wireless signal receiver.

4. The system of claim 2, further including a motion sensing device, the motion sensing device comprising a plurality of electrically isolated capacitors, an electrically conductive interior surface, an insulating layer, a variance detection member, a second amplifier, and a second analog-to-digital converter, the insulating layer disposed between the plurality of electrically isolated capacitors and the electrically conductive interior surface, the second amplifier configured to receive motion data from the variance detection member and transmit amplified motion data to the second analog-to-digital converter, and the second analog-to-digital converter configured to receive amplified motion data from the second amplifier and transmit digital contact data to the wireless signal receiver.

5. The system of claim 2, further including a speaker and a display device, the processor additionally programmed to transform the digital motion data and the digital contact data into graphic data and sound data, transmit the sound data to the speaker and transmit the graphic data to the display device.

6. A system including a motion sensing device, a processor, and a wireless signal receiver;

the mat comprising a plurality of electrically isolated capacitors, an electrically conductive interior surface, an insulating layer, a variance detection member, a second amplifier, and a second analog-to-digital converter, the insulating layer disposed between the plurality of electrically isolated capacitors and the electrically conductive interior surface, the second amplifier configured to receive motion data from the variance detection member and transmit amplified motion data to the second analog-to-digital converter, and the second analog-to-digital converter configured to receive amplified motion data from the second amplifier and transmit digital contact data to the wireless signal receiver;

the processor programmed to receive digital motion data and digital contact data from the wireless signal receiver, analyze the digital motion data and the digital contact data received from the wireless signal receiver, transform the digital motion data and the digital contact data into performance data, and transmit the performance data to a server; and the server configured to transfer local player events from a remote player site to another remote player site for presentation to another player, transmit turn notification data to remote player sites, receive and measure player time delays, disconnect player remotes sites with excessive time delays, and conduct an internet search for additional player remote sites.

7. The system of claim 6, further including a ball receptacle, the ball receptacle comprising an open end configured to receive a ball, a contact sensor, a first amplifier, and a first analog-to-digital converter, the contact sensor configured to transmit contact data to the first amplifier, the first amplifier configured to receive contact data from the contact sensor and transmit amplified contact data to the first analog-to-digital converter, and the first analog-to-digital converter configured to receive amplified contact data from the first amplifier and transmit digital contact data to the wireless signal receiver.

8. The system of claim 6, further including a sports implement, the sports implement comprising a hitting surface, a third amplifier, and a third analog-to-digital converter, the hitting surface comprising a transducer array, the transducer array including one or more piezoelectric elements, the transducer array configured to transmit contact data to the third amplifier, the third amplifier configured to receive contact data from the contact sensor and transmit amplified contact data to the third analog-to-digital converter, and the third analog-to-digital converter configured to receive amplified contact data from the third amplifier and transmit digital contact data to the wireless signal receiver.

9. The system of claim 6, further including a speaker and a display device, the processor additionally programmed to transform the digital motion data and the digital contact data into graphic data and sound data, transmit the sound data to the speaker, and transmit the graphic data to the display device.

10. The system of claim 6, further including a network of game systems, each game system being operated by a user.

* * * * *